Dec. 8, 1970 H. C. SWIM ET AL Plant Pat. 3,010
ROSE PLANT
Filed Jan. 27, 1969
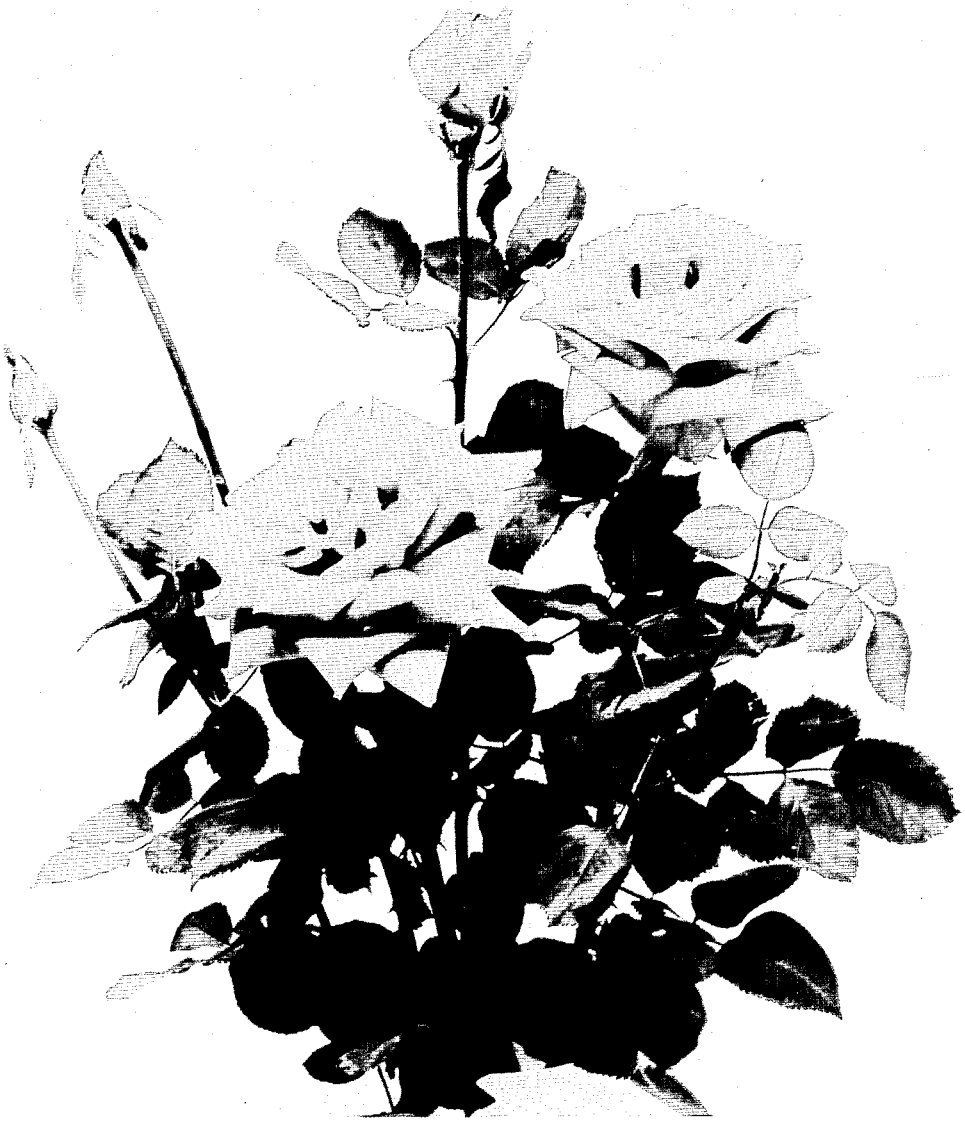
Inventors
H. C. Swim
J. L. Weeks
By: Robb & Robb
Attorneys.

United States Patent Office

Plant Pat. 3,010
Patented Dec. 8, 1970

3,010
ROSE PLANT

Herbert C. Swim and O. L. Weeks, Ontario, Calif., assignors to O. L. Weeks, doing business as Weeks Wholesale Rose Grower, Ontario, Calif.

Filed Jan. 27, 1969, Ser. No. 794,428
Int. Cl. A01h 5/00
U.S. Cl. Plt.—21 1 Claim The present invention relates to a new and distinct variety (cultivar) of rose plant of the Hybrid Tea class, which was originated by us by crossing the rose variety known as "Mister Lincoln" (Plant Pat. No. 2370) with the rose variety known as "Night 'n' Day" (Plant Pat. No. 2655).

As the result of this breeding, we have produce a new and improved rose variety which is distinguished from its parents, as well as from all other rose varieties of which we are aware, as evidenced by the following unique combination of characteristics which are outstanding in the new variety:

(1) An especially tall and vigorous plant habit, with stiff, long and erect stems which are clothed with persistent large foliage having average resistance to powdery mildew;
(2) A habit of bearing the flowers both singly and in clusters of up to five or sometimes more, with the individual stems in the clusters being unusually long and strong;
(3) A large flower size, with the flowers having excellent substance or petal stiffness which gives the flowers good lasting quality on the plant;
(4) An unusual deep dark reddish purple flower color;
(5) A strong damask-rose flower fragrance; and
(6) Better than average ability of the flowers to take up water as cut flowers, with consequent better than average vase-life when cut for indoor use.

In comparison with its seed parent "Mister Lincoln," the plants of the new variety are substantially taller and bushier than the plants of this parent; the flowers of the new variety are produced in greater abundance; the majority of the flowers of the new variety are borne in clusters and on quite long individual stems in each cluster, whereas the flowers of the parent variety are produced predominantly on an unbranched stem; the flowers are longer in relation to their width or breadth than those of "Mr. Lincoln," but are substantially smaller than those of this parent even though of large size; the flowers of the new variety have substantially greater substance or petal stiffness than those of "Mr. Lincoln;" and the flowers of the new variety are mor heavily pigmented, particularly in the reddish purple range than the flowers of this parent.

As compared with its pollen parent "Night 'n' Day," the plants of the new variety are substantially taller and more vigorous than the plants of this parent; the flowers of the new variety are popularly described as being deep reddish purple color, while those of this parent have little or no purple pigment and while being deep red in the bud stage, they open with a bright red center; and the flowers of the new variety are substantially more fragrant than those of this parent.

Asexual reproduction of our new variety by budding, as performed at Chino, Calif., shows that the aforementioned characteristics and distinctions come true to form and are established and transmitted through succeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Md., except where general color terms of ordinary dictionary significance are obvious:

Type: Tall; bush; outdoor; seeding; for cut flowers and/or garden decoration.
Class: Hybrid tea.
Breeding: Seedling.
*Seed parent.*—"Mister Lincoln."
*Pollen parent.*—"Night 'n' Day."
Propagation: Holds its distinguishing characteristics through succeeding propagations by budding.

*Flower*

Locality where grown and observed: Chino, Calif.
Flowers borne: Both singly and up to five or more to stem in irregular clusters; on strong and long stems.
Quantity of bloom: Free, both outdoors and in greenhouse.
Continuity: From intermittently to nearly continuous.
Fragrance: Strong.
*Nature.*—Damask.
Bud:
*Peduncle.*—Medium long; medium heavy caliper; erect; stiff; smooth except for few small prickles.
*Color.*—Yellowish green.
Before calyx breaks:
*Size.*—From medium to large.
*Form.*—Medium length; pointed; ovoid; with foliaceous appendages on the surface of the bud; with foliaceous parts extending beyond the tip of the bud equal to its length.
As calyx breaks—
*Color.*—Near Dark Red, Plate 2.5 R 3/7, but somewhat lighter at base.
As first petal opens—
*Size.*—From medium to large.
*Form.*—Pointed ovoid.
*Color.*—Outside—Primarily between Strong Purplish Red, Plate 10 RP 4/12 and Strong Purplish Red, Plate 10 RP 5/12, with central part of petal near Deep Purplish Pink, Plate 7.5 RP 6/12, and with base near Brilliant Greenish Yellow, Plate 7.5 Y 9/8. Inside—Between Deep Purplish Red, Plate 10 RP 3/10 and Srong Purplish Red, Plate 10 RP 4/12, but with base near Brilliant Greenish Yellow, Plate 7.5 Y 9/8 and often along midrib which is dominated by a vegetative streak of varying width and length.
Opening—
Opens up well; is not retarded by cold, hot, wet or dry weather.
Bloom:
*Size* (when fully open).—From medium to large; from 5 inches to 5½ inches.
*Petalage.*—From double to very double; usually with no stamens showing; from 45 to 50 petals, plus a varying number of usually small petaloids; arranged regularly.
*Form.*—High-centered at first and remaining high-centered; petals being at first loosely rolled outward, but later becoming more tightly rolled outward at maturity.
Petals:
*Texture.*—Thick; leathery.
*Appearance.*—Inside—Velvety. Outside—Shiny.

*Shape.*—Outside—Very broadly obovate, with apex entire. Intermediate—Obovate, with apex entire. Inside—Obovate, with apex entire.

This description of a newly opened flower was made from a rose grown in a greenhouse during the month of May at Chino, Calif.:

*Color.*—Outer petal: Outside surface—Primarily between Strong Purplish, Red Plate 10 RP 4/12 and Strong Purplish Red, Plate 10 RP 5/12, with central part of petal near Deep Purplish Pink, Plate 7.5 RP 6/12, and with base being Brilliant Greenish Yellow, Plate 7.5 Y 9/8. Inside surface—Between Deep Purplish Red, Plate 10 RP 3/10 and Strong Purplish Red, Plate 10 RP 4/12, except at base which is Brilliant Greenish Yellow, Plate 7.5 Y 9/8 and along midrib which is often dominated by a vegetative streak of varying width and length. Intermediate petal: Outside surface—Between Strong Purplish Red, Plate 7.5 RP 4/11 and Strong Purplish Red, Plate 10 RP 4/12, except at base which is Brilliant Greenish Yellow, Plate 7.5 Y 9/8. Inside surface—Near Strong Purplish Red, Plate 10 RP 4/12, paling toward base which becomes Brilliant Greenish Yellow, Plate 7.5 Y 9/8. Inner petal: Outside surface—Between Strong Purplish Red, Plate 7.5 RP 4/11 and Strong Purplish Red, Plate 10 RP 4/12, except at base which is Brilliant Greenish Yellow, Plate 7.5 Y 9/8. Inside surface—Near Strong Purplish Red, Plate 10 RP 4/12, paling toward base which becomes Brilliant Greenish Yellow, Plate 7.5 Y 9/8.

This description was made from a rose that was open for three days in a greenhouse during the month of May at Chino, Calif.:

Color.—Outer petal: Outside surface—Between Strong Purplish Red, Plate 7.5 RP 4/11 and Strong Purplish Red, Plate 7.5 RP 5/12, except at base where color is Brilliant Greenish Yellow, Plate 7.5 Y 9/8 and sometimes in area of midrib where color may be Strong Purplish Pink, Plate 7.5 RP 7/10 intermingled with greenish white. Inside surface—Near Strong Purplish Red, Plate 7.5 RP 4/11, except for vegetative streak of varying dimensions and shapes along midrib and at base which is near Brilliant Yellow, Plate 2.5 Y 9/9. Inner petal: Outside surface—Dominant color of petal is between Strong Purplish Red, Plate 7.5 RP 4/11 and Strong Purplish Red, Plate 7.5 RP 5/12, with base Brilliant Greenish Yellow, Plate 7.5 Y 9/8. Inside surface—Upper part of petal between Moderate Red, Plate 2.5 R 4/10 and Strong Purplish Red, Plate 10 RP 4/12, with lower portion paling to near Strong Purplish Red, Plate 10 RP 5/12, and with base near Brilliant Yellow, Plate 2.5 Y 9/9.

*General color effect.*—Newly opened flower—Near Deep Purplish Red, Plate 10 RP 3/10, but tending toward Dark Red, Plate 2.5 R 3/7. 3-days open—Near Deep Purplish Red, Plate 10 RP 3/10, but tending toward Dark Red, Plate 2.5 Y 3/7.

*Behavior.*—Drop off cleanly.

*Flower longevity.*—Cut roses grown in greenhouse and kept at living-room temperatures—5 day in May.

*Reproductive organs*

Stamens: From few to medium number; arranged irregularly about pistils; mixed with petaloids.

Filaments: Medium length.

*Color.*—From reddish to pink.

Anthers: Medium size; all open at once.

*Color.*—Yellow.

Pollen: Moderate quantity.

*Color.*—Yellow.

Pistils: Many.

Styles: Uneven; long; medium caliper; loosely bunched.

Stigma:

*Color.*—White.

Ovaries: All protruding from Calyx.

Hips: None observed.

Sepals: Permanent; curled or recurved.

Seeds: None observed; rarely sets seed.

*Plant*

Foliage:

*Leaflets*—Shape—Laterals ovoid; terminals broadly abundance; large size; moderately leathery.

*Leaflets.*—Shape—Laterals ovoid; terminals broadly ovoid. Apex—From acute to acuminate. Base—Round on terminals and laterals acute. Margin—Simply serrate.

*Color.*—Mature: Upper surface—Dark Green. Under surface—Normal Grey-green. Young: Upper surface—Light green, with reddish purple overlay, especially on veins and midrib. Under surface—Light reddish purple.

*Rachis* (the supporting stem of the compound leaf).—Medium weight. Upper side—Grooved; lined with stipitate glands. Under side—Moderately prickly.

*Stipules.*—Moderately short; moderately narrow; with short points turning out at an angle of more than 45°.

*Disease resistance.*—Average resistance to powdery mildew, as determined by comparison with several dozen other commercial varieties grown in a greenhouse under comparable conditions at Chino, Calif.

Growth:

*Habit.*—Tall; bushy; upright; much branched.

*Growth.*—Very vigorous.

*Canes.*—From medium to heavy caliper.

*Main stems.*—Color—Dull grey greenish brown. Large prickles—Many; long; hooked downward; with long, broad base. Color—Grey-brown. Small prickles—Few. Color—Grey-brown. Hairs—None.

*Branches.*—Color-Dull grey-green. Large prickles—Many; long; hooked downward; with long, broad base. Color—Brown. Small prickles—Few. Color—Brown. Hairs—None.

*New shoots.*—Color—Reddish purple. Large prickles—Many; long; hooked downward; with long, broad base. Color—Reddish purple base, with light green tips. Small prickles—Few. Color—Reddish purple. Hairs—None.

*New shoots.*—Color—Reddish purple. Large prickles—Many; long; hooked dowwnard; with long, broad base. Color—Reddish purple base, with light green tips. Small prickles—Few. Color—Reddish purple. Hairs—None.

We claim:

A new and distinct variety of rose plant of the hybrid tea class, substantially as herein shown and described, characterized particularly as to novelty by the unique combinaion of an especially tall and vigorous plant habit, with stiff, long and erect stems which are clothed with persistent large foliage having average resistance to powdery mildew, a habit of bearing the flowers both singly and in clusters of up to five or sometimes more, with the individual stems in the clusters being unusually long and strong, a large flower size with the flowers having excellent substance or petal stiffness which gives the flowers good lasting quality on the plant, an unusual deep dark reddish purple flower color, a strong damask-rose flower fragrance, and better than average ability of the flowers to take up water as cut flowers, with consequent better than average vase-life when cut for indoor use.

No reference cited

ROBERT E. BAGWILL, Primary Examiner